(12) United States Patent
Xue et al.

(10) Patent No.: US 8,313,537 B2
(45) Date of Patent: Nov. 20, 2012

(54) MORDANT AND HAIR COLORING PRODUCTS CONTAINING THE SAME

(75) Inventors: Lian Xue, Zhejiang (CN); Liu Hu, Zhejiang (CN); Hongying Lan, Hangzhou (CN); Zhiming Huang, Hangzhou (CN); Yulan Liu, Hangzhou (CN); Yuhua Liao, Hangzhou (CN)

(73) Assignee: Natural Medicine Institute Of Zhejiang Yangshengtang Co. Ltd., Zhejiang (CN)

( * ) Notice: Subject to any disclaimer, the term of this patent is extended or adjusted under 35 U.S.C. 154(b) by 0 days.

(21) Appl. No.: 13/202,211

(22) PCT Filed: Jan. 27, 2010

(86) PCT No.: PCT/CN2010/000122
§ 371 (c)(1),
(2), (4) Date: Oct. 13, 2011

(87) PCT Pub. No.: WO2010/094207
PCT Pub. Date: Aug. 26, 2010

(65) Prior Publication Data
US 2012/0037178 A1 Feb. 16, 2012

(30) Foreign Application Priority Data

Feb. 20, 2009 (CN) .......................... 2009 1 0009172

(51) Int. Cl.
*A61Q 5/10* (2006.01)
(52) U.S. Cl. ............. 8/405; 8/425; 8/435; 8/460; 8/623; 132/202; 132/208
(58) Field of Classification Search ............... 8/405, 425, 8/435, 460, 623; 132/202, 208
See application file for complete search history.

(56) References Cited

FOREIGN PATENT DOCUMENTS

| | | | |
|---|---|---|---|
| CN | 1401310 | A | 3/2003 |
| CN | 1593375 | A | 3/2005 |
| JP | 53052633 | A | 5/1978 |
| JP | 5075700 | B | 10/1993 |
| JP | 2002138024 | A | 5/2002 |
| KR | 100812118 | B | 3/2008 |

OTHER PUBLICATIONS

English abstract of the JP Patent No. 53052633 A dated May 13, 1978.*
International Patent Application No. PCT/CN2010/000122: International Search Report dated May 6, 2010, 6 pages.

* cited by examiner

*Primary Examiner* — Eisa Elhilo
(74) *Attorney, Agent, or Firm* — Woodcock Washburn, LLP

(57) ABSTRACT

The present invention relates to a mordant for hair dyeing and a hair dyeing product comprising the mordant. The mordant of the present invention comprises an effective amount of a ferrous salt, antioxidant and water; the hair dyeing product of the present invention comprises three parts: a softening agent, a dyeing agent, and the mordant. The mordant and the hair dyeing product comprising the mordant as provided by the present invention do not contain thioglycolic acid, aromatic compounds such as p-phenylenediamine and hydrogen peroxide, and are safe and free of irritation. The hair dyeing product of the present invention has good chromaticity and fastness as well as good product stability and convenience in usage.

24 Claims, No Drawings

MORDANT AND HAIR COLORING PRODUCTS CONTAINING THE SAME

CROSS-REFERENCE TO RELATED APPLICATIONS

This application is the National Stage of International Application No. PCT/CN2010/000122, filed Jan. 27, 2010, which claims the benefit of Chinese Application No. 200910009172.4, filed Feb. 20, 2009, the disclosures of which are incorporated herein by reference in their entireties.

TECHNICAL FIELD

The present invention relates to the technical field of cosmetic industry, specifically relates to a mordant useful in a hair dyeing product. The present invention further relates to a hair dyeing product comprising the mordant, especially a non-oxidative, permanent natural hair darkening preparation comprising the mordant.

BACKGROUND ART

At present, most of hair dyeing products available from markets are oxidative hair dyeing products comprising thioglycolic acid as a penetration enhancing agent, aromatic amines such as p-phenylenediamine as a dye and hydrogen peroxide as an oxidant. Many studies and reports demonstrate that thioglycolic acid, p-phenylenediamine, hydrogen peroxide and the like all have certain toxicities and allergies. Hence, the development of hair dyeing products with a high safety is paid more and more attention. In recent years, many natural hair dyeing products are available from markets, but such products usually have the following two drawbacks: one is that some of so-called "purely natural" or "organic" hair dyeing products merely are added with some vegetative concept components, but still comprise harmful chemical substances such as p-phenylenediamine, so that long-term use thereof still produces relatively severe side-effects; and the other is that natural hair dyeing components usually are larger molecules so that it is difficult to dye and maintain the color permanently, and thus the hair dyeing effects, the stability of the products and convenience of application are still not satisfactory. In addition, it has been found that for some natural hair dyeing products such as those disclosed in CN1401310A (Chinese Patent Application No. 01127328.3, publication date) and CN1593375A (Chinese Patent Application No. 200410009258.4, publication date of 2005 Mar. 16), after being prepared and used according to the method disclosed therein, their hair dyeing effects, especially the effects of darkening white hairs are relatively poor, and the stability of their mordant components is not good, so that the final product contains relatively lower concentration of free iron ions which influences the hair dyeing effects of the products, specifically during their shelf life of the products. In addition, these products all need multiple hair washings and multiple applications before and during the hair dyeing procedures, which is less convenient for use. Therefore, there is still a need for developing purely natural hair dyeing products with good safety, coloring effects, stability and convenience.

CONTENTS OF THE INVENTION

The object of the present invention is to provide a non-oxidative, permanent, natural hair dyeing product, especially a hair darkening product. The inventors have found that a composition having specific components has satisfactory hair dyeing effects, and the present invention has been completed based this discovery.

SUMMARY OF THE INVENTION

In general, the present invention provides the following items:

1. A mordant for use in a hair dyeing product, comprising an effective amount of a ferrous salt and an antioxidant.

2. The mordant of item 1, wherein the ferrite salt is selected from the group consisting of ferrous sulfate, ferrous chloride, ferrous nitrate, ferrous gluconate, ferrous lactate, and ferrous fumarate.

3. The mordant of item 2, wherein the ferrous salt constitutes 0.5-10% (wt) of the total weight of the mordant.

4. The mordant of item 1, wherein the antioxidant is selected from the group consisting of ascorbic acid or salts thereof, cysteine or derivatives thereof and salts thereof, such as ascorbic acid, sodium ascorbate, cysteine, cysteine hydrochloride, N-acetylcysteine, a reduced glutathione, such as D-cysteine, L-cysteine, DL-cysteine, N-acetylcysteine, and salts thereof.

5. The mordant of item 4, wherein the antioxidant constitutes 0.1-2% (wt) of the total weight of the mordant.

6. The mordant of any one of items 1 to 5, further comprising one or more components selected from the group consisting of: water, a penetration enhancing agent, a thickening agent, and a preservative.

7. A hair dyeing product, comprising the following three parts: a softening agent, a dyeing agent, and the mordant of any one of items 1 to 6.

8. The hair dyeing product of item 7, wherein the dyeing agent comprises an effective amount of an active dye substance and optionally water.

9. The hair dyeing product of item 8, wherein the active dye substance in the dyeing agent is selected from the group consisting og gallic acid and salts or esters thereof, such as gallic acid and methyl ester, ethyl ester or propyl ester of gallic acid, and any combination thereof.

10. The hair dyeing product of item 9, wherein the active dye substance in the dyeing agent constitutes 0.5-15% (wt) of the total weight of the dyeing agent.

11. The hair dyeing product of item 8, wherein the dyeing agent further comprises one or more components selected from the group consisting of: a stabilizing agent, a penetration enhancing agent, and a thickening agent.

12. The hair dyeing product of any one of items 7 to 11, wherein the softening agent comprises an effective amount of a disulfide bond reducing agent and an alkalizing agent.

13. The hair dyeing product of item 12, characterized in that:
i) the disulfide bond reducing agent in the softening agent is selected from the group consisting of cysteine or derivatives thereof and their salts, urea, thiosulfates, a sulfite, and a bisulfate, and any combination thereof;
ii) the alkalizing agent in the softening agent is selected from the group consisting of ornithine, arginine, lysine, ammonia, an ethanolamine (such as monoethanolamine, diethanolamine, or triethanolamine), an alkanolamide, a hydroxide or a composition comprising a carbonate, and any combination thereof; and/or
iii) the softening agent further comprises one or more components selected from the group consisting of: water, a penetration enhancing agent, and a thickening agent.

14. The hair dyeing product of any one of items 7 to 13, further comprising an information material regarding the method for using the hair dyeing product.

15. The hair dyeing product of item 14, wherein the information material at least comprises the following information:

a) a step of treating the hair by applying the softening agent to the hair; and b) a step of treating the hair by applying the mordant and the dyeing agent to the hair in any order.

16. The hair dyeing product of item 14, wherein the information material comprises at least one of the following items i to iii of information:

i (1) a step of treating the hair by applying the softening agent to the hair; and (2) a step of treating the hair by mixing the mordant and the dyeing agent before use and then applying the mixture to the hair; or ii (1) a step of treating the hair by mixing the softening agent and the mordant before use and then applying the mixture to the hair; and (2) a step of treating the hair by applying the dyeing agent to the hair; or iii (1) a step of treating the hair by mixing the softening agent and the dyeing agent before use and then applying the mixture to the hair; and (2) a step of treating the hair by applying the mordant to the hair.

17. A dyeing agent, comprising an effective amount of an active dye substance, and optionally one or more components selected from the group consisting of: water, a stabilizing agent, a penetration enhancing agent, and a thickening agent.

18. The dyeing agent of item 17, wherein the active dye substance is selected from the group consisting of gallic acid and salts or esters thereof, for example, gallic acid, and methyl ester, ethyl ester, or propyl ester of gallic acid, and any combination thereof.

19. A method for dyeing hair by using the hair dyeing product of any one of items 7 to 16, comprising:

a) a step of treating the hair by applying the softening agent to the hair; and b) a step of treating the hair by applying the mordant and the dyeing agent to the hair in any order.

20. A method for dyeing hair by using the hair dyeing product of any one of items 7-16, comprising at least one of the following steps i to iii:

I (1) a step of treating the hair by applying the softening agent to the hair; and (2) a step of treating the hair by mixing the mordant and the dyeing agent before use and then applying the mixture to the hair; or ii (1) a step of treating the hair by mixing the softening agent and the mordant before use and then applying the mixture to the hair; and (2) a step of treating the hair by applying the dyeing agent to the hair; or iii (1) a step of treating the hair by mixing the softening agent and the dyeing agent before use and then applying the mixture to the hair; and (2) a step of treating the hair by applying the mordant to the hair.

DETAILED DESCRIPTION OF THE INVENTION

The entire contents of all the cited documents are incorporated herein by reference, and when there are inconsistencies between the documents and the present invention, the expressions of the present invention should be used. In addition, the terminologies and phrases used in the present invention have their general meanings as well known by those skilled in the art. However, it is still intends to provide descriptions and explanations for these terminologies and phrases in more details in the present invention, and when the meanings of terms and phrases as mentioned in the present invention are not consistent with those well-known in the art, the meanings as mentioned in the present invention should be used.

The object of the present invention is to provide a non-oxidative, permanent, natural hair dyeing product, especially a hair darkening product. This natural hair dyeing product not only is safe and free of irritation as well as good in chromaticity and fastness, but also has a good stability and usability. The inventors have found that a stable mordant can be obtained by using a ferrous salt as the active component of the mordant; and that gallic acid naturally existing in tannin is well safe as a dye, and forms a complex with iron ions in hair to achieve a good chromaticity and fastness of the dyed hair. Hence, the present invention firstly provides a mordant for use in a hair dyeing product, which is featured with a good stability; and the present invention also provides a hair dyeing product comprising the mordant.

Gallic acid is a monomer of the hydrolysable tannin in tannins, naturally exists in tannins and has a structure as follows:

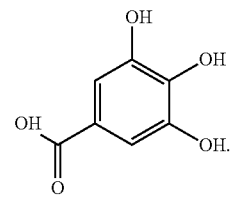

Gallic acid has a molecular weight of 170.12, and is used as an astringent and a hemostat in medicine. Gallic acid is in the form of a white or amber needle crystal powder. Since there is a plurality of ortho phenolic hydroxyl groups in the molecular structure, gallic acid can be used as a multiple-hydroxy ligand in a complexation reaction with iron ion to form a black stable compact chelate-iron gallate. According to the present invention, esters of gallic acid can also be used, and the esters of gallic acid are compounds with an ester structure derived from the carboxylic group of gallic acid.

In general, the outer layer of hair is covered by hair scales consisting of multilayer keratin, so that the penetration of gallic acid and metal ions is poor. In one example of the present invention, acetylcysteine can be used as a disulfide bond reducing agent (sometimes referred to herein as a "penetration enhancing agent") to reduce —S—S— of cuticular keratin as —SH so as to soften hair, release tension, open hair scales in some extent to allow ferrous ions enter cortical layer and medulla layer in the hair, then ferrous ions are oxidized by air to form ferric ions which complex with gallic acid penetrated inside hair to form a black dye macromolecule,

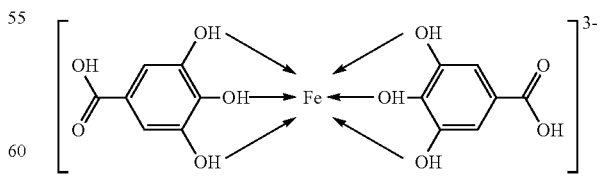

so as to provide the hair black color, and form a permanent hair dyeing product after hair scales close.

Generally, the first aspect of the present invention provides a mordant for ues in a hair dyeing product, comprising an effective amount of a ferrous salt, and an antioxidant.

The mordant according to any item of the first aspect of the present invention further comprises water. The amount of water can be for example a suitable amount added during the preparation of mordant, and the suitable amount is capable of achieving the expected and/or predetermined concentration of main components in the mordant. In addition, although the mordant of the present invention can be free of water, the preferred embodiments of the present invention provide either a mordant already formulated in water for convenience in usage, for example a ready-to-use mordant that can be directly used without any post treatments, or a concentrated mordant that needs to be diluted before use.

According to the mordant of any item of the first aspect of the present invention, the ferrous salt includes but is not limited to ferrous sulfate, ferrous chloride, ferrous nitrate, ferrous gluconate, ferrous lactate, and ferrous fumarate and the like. In one embodiment of the mordant of the present invention, the ferrous salt is selected from the group consisting of ferrous sulfate and ferrous chloride. In another embodiment of the mordant of the present invention, the ferrous salt is ferrous sulfate. According to the mordant of the present invention, the ferrous salt can be a single ferrous salt or any combination of a plurality of ferrous salts. According to the mordant of any item of the first aspect of the present invention, the ferrous salt constitutes 0.5-10% (wt) of the total weight of the mordant. In an embodiment of the mordant of the present invention, the ferrous salt constitutes 2-8% (wt) of the total weight of the mordant.

According to the mordant of any item of the first aspect of the present invention, the antioxidant includes but is not limited to ascorbic acid or salts thereof, and cysteine or derivatives thereof and salts thereof, such as ascorbic acid, sodium ascorbate, cysteine, cysteine hydrochloride, N-acetylcysteine, reduced glutathione, etc. In an embodiment of the mordant of the present invention, the antioxidant is selected from cysteine or derivatives thereof and salts thereof. In an embodiment of the mordant of the present invention, the antioxidant is selected from D-cysteine, L-cysteine, DL-cysteine, N-acetylcysteine, and salts thereof. In an embodiment of the mordant of the present invention, the antioxidant is selected from cysteine hydrochloride. In an embodiment of the mordant of the present invention, the antioxidant is a single antioxidant, or any combination of a plurality of antioxidants. According to the mordant of any item of the first aspect of the present invention, the antioxidant constitutes 0.1-2% (wt) of the total weight of the mordant. In an embodiment of the mordant of the present invention, the antioxidant constitutes 0.2-1% (wt) of the total weight of the mordant.

The mordant according to any item of the first aspect of the present invention further comprises a penetration enhancing agent (i.e., penetration enhancer). In an embodiment of the mordant of the present invention, the penetration enhancing agent includes but is not limited to a chemical penetration enhancing agent: azones and homologues thereof, organic acids and esters thereof, organic solvents, surfactants such as anionic surfactants, nonionic surfactants and ampholytic surfactants; Chinese medicine penetration enhancing agents: including terpenes, essential oils and lactones; and any combinations thereof. In an embodiment of the mordant of the present invention, the penetration enhancing agent can be selected from the group consisting of: oleyl alcohols, dodecylsulfate, dodecylsulfonate or other anionic surfactants, nonionic surfactants such as fatty alcohol ethers, cocamidopropyl betaine or other ampholytic surfactants, and any combination thereof. In an embodiment of the mordant of the present invention, the penetration enhancing agent can be a single or a mixture of oleyl alcohol, dodecylsulfate or other anionic surfactants, nonionic surfactants such as fatty alcohol ethers, cocamidopropyl betaine or other ampholytic surfactants. According to the mordant of the present invention, the penetration enhancing agent can be a single penetration enhancing agent, or any combination of a plurality of penetration enhancing agents. In an embodiment of the mordant of the present invention, the penetration enhancing agent constitutes 1-10% (wt) of the total weight of the mordant. In an embodiment of the mordant of the present invention, the penetration enhancing agent constitutes 2-8% (wt) of the total weight of the mordant.

The mordant according to any item of the first aspect of the present invention further comprises a thickening agent (i.e., a viscosity regulator for regulating the state of fluid such as liquid, semi-solid, etc.). In an embodiment of the mordant of the present invention, the thickening agent includes but is not limited to one or more of fatty alcohols or polymers such as carbomers, hydroxyethylcellulose, and hydroxypropylcellulose. In an embodiment of the mordant of the present invention, the weight percentage of the thickening agent in the mordant can be determined by those skilled in the art according to the teachings of the present application in combination with the prior art. Preferably, in an embodiment of the mordant of the present invention, the thickening agent constitutes 1-10% (wt) of the total weight of the mordant. In an embodiment of the mordant of the present invention, the thickening agent constitutes 2-8% (wt) of the total weight of the mordant.

The mordant according to any item of the first aspect of the present invention further comprises a preservative. In an embodiment of the mordant of the present invention, the preservative includes but is not limited to parabens, such as methyl paraben, ethyl paraben, propyl paraben and butyl paraben. The preservative can be a single preservative or any combination of a plurality of preservatives, such as a combination of methyl paraben and ethyl paraben in any ratio. In an embodiment of the mordant of the present invention, the weight percentage of the preservative in the mordant can be determined by those skilled in the art according to the teachings of the present application in combination with the prior art. Preferably, in an embodiment of the mordant of the present invention, the preservative constitutes 0.1-0.8% (wt) of the total weight of the mordant. In an embodiment of the mordant of the present invention, the preservative constitutes 0.2-0.6% (wt) of the total weight of the mordant.

The mordant of any item of the first aspect of the present invention is present in the form of an emulsion, paste or gel.

The second aspect of the present invention provides a hair dyeing product, comprising the following three parts: a softening agent (conveniently referred to herein as the first component), a dyeing agent (conveniently referred to herein as the third component), and the mordant of any item of the first aspect of the present invention (conveniently referred to herein as the second component). According to the present invention, the three parts are preferably physically independent, and are used in certain order when they are used for dyeing hair. Hence, in some senses, the hair dyeing product of the present invention can also be a multi-component hair dyeing product.

According to the hair dyeing product of any item of the second aspect of the present invention, the dyeing agent comprises an effective amount of an active dye substance. According to the hair dyeing product of any item of the second aspect of the present invention, the dyeing agent can further comprises water. The amount of water can be for example a suitable amount as added when preparing, and the suitable amount allows the main components of the dyeing agent to reach a predetermined concentration. In addition, although the dyeing agent as provided in the present invention can be free of water, the preferred embodiments of the present invention provide either a dyeing agent already formulated in water for convenience in usage, for example a ready-to-use dyeing agent that can be directly used without any post treatments, or a concentrated dyeing agent that needs to be diluted before use.

In an embodiment of the hair dyeing product of the second aspect of the present invention, the active dye substance in the dyeing agent includes but is not limited to gallic acid and salts or esters thereof or any combination thereof. The esters of gallic acid can be for example methyl gallate, ethyl gallate or propyl gallate. In an embodiment of the hair dyeing product of the second aspect of the present invention, the active dye substance in the dyeing agent is gallic acid. In an embodiment of the hair dyeing product of the present invention, the active dye substance in the dyeing agent constitutes 0.5-15% (wt) of the total weight of the dyeing agent. In an embodiment of the hair dyeing product of the present invention, the active dye substance in the dyeing agent constitutes 1-10% (wt) of the total weight of the dyeing agent.

According to the hair dyeing product of any item of the second aspect of the present invention, the dyeing agent further comprises a stabilizing agent for keeping the active dye substance stable, the stabilizing agent includes but is not limited to one or more of EDTA-Na, a sulfite, a bisulfite, ascorbates, cysteine and salts or derivatives thereof. In an embodiment of the hair dyeing product of the present invention, the weight percentage of the stabilizing agent in the dyeing agent can be determined by those skilled in the art according to the teachings of the present application in combination with the prior art. Preferably, in an embodiment of the hair dyeing product of the present invention, the stabilizing agent constitutes 0.1-1.5% (wt) of the total weight of the dyeing agent. In an embodiment of the hair dyeing product of the present invention, the stabilizing agent constitutes 0.2-1% (wt) of the total weight of the dyeing agent.

According to the hair dyeing product of any item of the second aspect of the present invention, the dyeing agent further comprises a penetration enhancing agent (i.e., penetration enhancer). In an embodiment of the hair dyeing product of the present invention, the penetration enhancing agent in the dyeing agent includes but is not limited to a chemical penetration enhancing agent: azones and homologues thereof, organic acids and esters thereof, organic solvents, surfactants such as anionic surfactants, nonionic surfactants, and ampholytic surfactants; Chinese medicine penetration enhancing agents: including terpenes, essential oils and lactones; and any combinations thereof. In an embodiment of the hair dyeing product of the present invention, the penetration enhancing agent in the dyeing agent can be selected from the group consisting of: oleyl alcohols, dodecylsulfate, dodecylsulfonate or other anionic surfactants, nonionic surfactants such as fatty alcohol ethers, cocamidopropyl betaine or other ampholytic surfactants, and any combination thereof. In an embodiment of the hair dyeing product of the present invention, the penetration enhancing agent in the dyeing agent can be a single or a mixture of oleyl alcohol, dodecylsulfate or other anionic surfactants, nonionic surfactants such as fatty alcohol ethers, cocamidopropyl betaine or other ampholytic surfactants. According to the hair dyeing product of the present invention, the penetration enhancing agent in the dyeing agent can be a single penetration enhancing agent, or any combination of a plurality of penetration enhancing agents. In an embodiment of the hair dyeing product of the present invention, the penetration enhancing agent in the dyeing agent constitutes 2-15% (wt) of the total weight of the dyeing agent. In an embodiment of the hair dyeing product of the present invention, the penetration enhancing agent constitutes 3-10% (wt) of the total weight of the dyeing agent.

According to the hair dyeing product of any item of the second aspect of the present invention, the dyeing agent further comprises a thickening agent (i.e., a viscosity regulator for regulating the state of fluid such as liquid, semi-solid, etc.). In an embodiment of the hair dyeing product of the present invention, the thickening agent in the dyeing agent includes but is not limited to one or more of fatty alcohols or polymers such as carbomers, hydroxyethylcellulose, and hydroxypropylcellulose. In an embodiment of the hair dyeing product of the present invention, the weight percentage of the thickening agent in the dyeing agent can be determined by those skilled in the art according to the teachings of the present application in combination with the prior art. Preferably, in an embodiment of the hair dyeing product of the present invention, the thickening agent in the dyeing agent constitutes 1-10% (wt) of the total weight of the dyeing agent. In an embodiment of the hair dyeing product of the present invention, the thickening agent in the dyeing agent constitutes 2-8% (wt) of the total weight of the dyeing agent.

According to the hair dyeing product of any item of the second aspect of the present invention, the dyeing agent is present in the form of emulsion, paste or gel.

According to the hair dyeing product of any item of the second aspect of the present invention, the softening agent comprises an effective amount of a disulfide bond reducing agent, and an alkalizing agent. According to the hair dyeing product of any item of the second aspect of the present invention, the softening agent can further comprise water. The amount of water can be for example a suitable amount added during preparing, and the suitable amount is capable of achieving the predetermined concentration of main components in the softening agent. In addition, although the softening agent as provided in the present invention can be free of water, the preferred embodiments of the present invention provide either a softening agent already formulated in water for convenience in usage, for example a ready-to-use softening agent that can be directly used without any post treatments, or a concentrated softening agent that needs to be diluted before use.

In an embodiment of the hair dyeing product of the second aspect of the present invention, the disulfide bond reducing agent in the softening agent includes but is not limited to cysteine or derivatives thereof and their salts, urea, thiosulfates, a sulfite, and a bisulfate, or any combination thereof. In an embodiment of the hair dyeing product of the second aspect of the present invention, the disulfide bond reducing agent in the softening agent is selected from acetylcysteine or salts thereof, cysteine or hydrochloride thereof, reduced glutathione, a sulfite, and a bisulfite. In an embodiment of the hair dyeing product of the present invention, the disulfide bond reducing agent in the softening agent constitutes 2-25% (wt) of the total weight of the softening agent. In an embodiment of the hair dyeing product of the present invention, the disulfide bond reducing agent in the softening agent constitutes 4-15% (wt) of the total weight of the softening agent.

In an embodiment of the hair dyeing product of the second aspect of the present invention, the alkalizing agent in the softening agent is selected from the group consisting of: ornithine, arginine, lysine, ammonia, an ethanolamine (such as monoethanolamine, diethanolamine, or triethanolamine), an alkanolamide, a hydroxide or a composition comprising a carbonate, and any combination thereof. In an embodiment of the hair dyeing product of the present invention, the alkalizing agent in the softening agent constitutes 0.5-20% (wt) of the total weight of the softening agent. In an embodiment of the hair dyeing product of the present invention, the alkalizing agent in the softening agent constitutes 2-18% (wt) of the total weight of the softening agent According to the hair dyeing product of any item of the second aspect of the present invention, the softening agent further comprises a penetration enhancing agent (i.e., penetration enhancer). In an embodiment of the hair dyeing product of the present invention, the penetration enhancing agent in the softening agent includes but is not limited to chemical penetration enhancing agents: azones and homologues thereof, organic acids and esters thereof, organic solvents, surfactants such as anionic surfactants, nonionic surfactants, and ampholytic surfactants; Chinese medicine penetration enhancing agents: including terpenes, essential oils and lactones; and any combinations thereof. In an embodiment of the hair dyeing product of the present invention, the penetration enhancing agent in the softening agent can be selected from the group consisting of: oleyl alcohols, dodecylsulfate, dodecylsulfonate or other anionic surfactants, nonionic surfactants such as fatty alcohol ethers, cocamidopropyl betaine or other ampholytic surfactants, and any combination thereof. In an embodiment of the hair dyeing product of the present invention, the penetration enhancing agent in the softening agent can be a single or a mixture of oleyl alcohol, dodecylsulfate or other anionic surfactants, nonionic surfactants such as fatty alcohol ethers, cocamidopropyl betaine or other ampholytic surfactants. According to the hair dyeing product of the present invention, the penetration enhancing agent in the softening agent can be a single penetration enhancing agent, or any combination of a plurality of penetration enhancing agents. According to the hair dyeing product of the present invention, the penetration enhancing agent in the softening agent can be one or more in combination of components selected from the group consisting of: sodium dodecylsulfate, sodium laureth sulfate, cocamidopropyl betaine. In an embodiment of the hair dyeing product of the present invention, the penetration enhancing agent in the softening agent constitutes 1-10% (wt) of the total weight of the softening agent. In an embodiment of the hair dyeing product of the present invention, the penetration enhancing agent constitutes 2-8% (wt) of the total weight of the softening agent.

According to the hair dyeing product of any item of the second aspect of the present invention, the softening agent further comprises a thickening agent (i.e., a viscosity regulator for regulating the state of fluid such as liquid, semi-solid, etc.). In an embodiment of the hair dyeing product of the present invention, the thickening agent in the softening agent includes but is not limited to one or more of fatty alcohols or polymers such as carbomers, hydroxyethylcellulose, and hydroxypropylcellulose. In an embodiment of the hair dyeing product of the present invention, the weight percentage of the thickening agent in the softening agent can be determined by those skilled in the art according to the teachings of the present application in combination with the prior art. Preferably, in an embodiment of the hair dyeing product of the present invention, the thickening agent in the softening agent constitutes 0.1-2% (wt) of the total weight of the softening agent. In an embodiment of the hair dyeing product of the present invention, the thickening agent in the softening agent constitutes 0.2-1% (wt) of the total weight of the softening agent.

According to the hair dyeing product of any item of the second aspect of the present invention, the softening agent is present in the form of emulsion, paste or gel.

The hair dyeing product of any item of the second aspect of the present invention further comprises an information material regarding the method for using the hair dyeing product. In an embodiment, the information material is selected from an instruction of product, a guideline for use, a technical description, and a leaflet, etc.

According to the hair dyeing product of any item of the second aspect of the present invention, the information material at least comprises the following information:

a) a step of treating the hair by applying the softening agent to the hair; and b) a step of treating the hair by applying the mordant and the dyeing agent to the hair in any order.

According to the hair dyeing product of any item of the second aspect of the present invention, the item a) of the information material further comprises: keeping the softening agent at a suitable temperature for a suitable period of time after it is applied to the hair. In an embodiment, the item a) of the information material further comprises: keeping the softening agent at 15-60° C. (preferably 20-40° C.) for 5-60 min (preferably 20-40 min, preferably 20-30 min) after it is applied to the hair.

According to the hair dyeing product of any item of the second aspect of the present invention, the item b) of the information material further comprises: keeping the mordant at a suitable temperature for a suitable period of time after it is applied to the hair. In an embodiment, the item b) of the information material further comprises: keeping the mordant at 15-60° C. (preferably 20-40° C.) for 5-60 min (preferably 20-40 min, preferably 20-30 min) after it is applied to the hair.

According to the hair dyeing product of any item of the second aspect of the present invention, the item b) of the information material further comprises: keeping the dyeing agent at a suitable temperature for a suitable period of time after it is applied to the hair. In an embodiment, the item b) of the information material further comprises: keeping the dyeing agent at 15-60° C. (preferably 20-40° C.) for 5-60 min (preferably 5-35 min, preferably 8-20 min) after it is applied to the hair.

According to the hair dyeing product of any item of the second aspect of the present invention, the information material comprises at least one of the following items i to iii of information:

i (1) a step of treating the hair by applying the softening agent to the hair; and (2) a step of treating the hair by mixing the mordant and the dyeing agent before use and then applying the mixture to the hair; or ii (1) a step of treating the hair by mixing the softening agent and the mordant before use and then applying the mixture to the hair; and (2) a step of treating the hair by applying the dyeing agent to the hair; or iii (1) a step of treating the hair by mixing the softening agent and the dyeing agent before use and then applying the mixture to the hair; and (2) a step of treating the hair by applying the mordant to the hair.

In each of the items i to iii of information, the step (1) comprises: keeping the softening agent, the mixture of the softening agent and the mordant, or the mixture of the softening agent and the dyeing agent at 15-60° C. (preferably 20-40° C.) for 10-40 min (preferably 15-35 min, preferably 20-30 min) after it is applied to the hair.

In each of the items i to iii of information, the step (2) comprises: keeping the mixture of the mordant and the dyeing agent, the dyeing agent, or the mordant at 15-60° C. (preferably 20-40° C.) for 2-30 min (preferably 5-25 min, preferably 10-20 min) after it is applied to the hair.

According to the hair dyeing product of any item of the second aspect of the present invention, the information material further comprises one or more of following items of information:
- a step of treating the hair by repeatedly applying uniformly the softening agent to the hair, and an optional step of washing the hair with water after the treatment;
- a step of treating the hair by repeatedly applying uniformly the mordant to the hair, and an optional step of washing the hair with water after the treatment;
- a step of treating the hair by repeatedly applying uniformly the dyeing agent to the hair, and an optional step of washing the hair with water after the treatment;
- a step of treating the hair by repeatedly applying uniformly the mixture of the softening agent and the dyeing agent to the hair, and an optional step of washing the hair with water after the treatment;
- a step of treating the hair by repeatedly applying uniformly the mixture of the softening agent and the mordant to the hair, and an optional step of washing the hair with water after the treatment;
- a step of treating the hair by repeatedly applying uniformly the mixture of the mordant and the dyeing agent to the hair, and an optional step of washing the hair with water after the treatment.

According to the hair dyeing product of the second aspect of the present invention, a dyeing agent based on the dyeing agent of the hair dyeing product is also provided. Hence, the third aspect of the present invention provides a dyeing agent useful in a hair dyeing product, comprising an effective amount of an active dye substance. The dyeing agent of any item of the third aspect of the present invention further comprises water. The amount of water can be for example a suitable amount added during preparing, and the suitable amount is capable of achieving the predetermined concentration of main components in the dyeing agent. In addition, although the dyeing agent as provided by the present invention can be free of water, the preferred embodiments of the present invention provide a dyeing agent already formulated in water for convenience in usage, for example a ready-to-use mordant that can be directly used without any post treatments, or a concentrated mordant that can be diluted before use.

In an embodiment of the dyeing agent of the third aspect of the present invention, the active dye substance includes but is not limited to gallic acid and salts or esters thereof, or any combination thereof. The esters of gallic acid can be for example methyl gallate, ethyl gallate or propyl gallate. In an embodiment of the dyeing agent of the third aspect of the present invention, the active dye substance is gallic acid. In an embodiment of the dyeing agent of the third aspect of the present invention, the active dye substance constitutes 0.5-15% (wt) relative to the total weigh of the dyeing agent. In an embodiment of the dyeing agent of the third aspect of the present invention, the active dye substance constitutes 1-10% (wt) of the total weight of the dyeing agent.

The dyeing agent according to any item of the third aspect of the present invention further comprises a stabilizing agent for keeping the active dye substance stable, the stabilizing agent includes but is not limited to one or more of EDTA-Na, a sulfite, and a bisulfite, ascorbates, cysteine and salts or derivatives thereof. In an embodiment of the dyeing agent of the present invention, the weight percentage of the stabilizing agent in the dyeing agent can be determined by those skilled in the art according to the teachings of the present application in combination with the prior art. Preferably, in an embodiment of the dyeing agent of the present invention, the stabilizing agent constitutes 0.1-1.5% (wt) of the total weight of the dyeing agent. In an embodiment of the dyeing agent of the present invention, the stabilizing agent constitutes 0.2-1% (wt) of the total weight of the dyeing agent.

The dyeing agent according to any item of the third aspect of the present invention further comprises a penetration enhancing agent (i.e., penetration enhancer). In an embodiment of the dyeing agent of the present invention, the penetration enhancing agent includes but is not limited to chemical penetration enhancing agents: azones and homologues thereof, organic acids and esters thereof, organic solvents, surfactants such as anionic surfactants, nonionic surfactants, and ampholytic surfactants; Chinese medicine penetration enhancing agents: including terpenes, essential oils and lactones; and any combinations thereof. In an embodiment of the dyeing agent of the present invention, the penetration enhancing agent can be selected from the group consisting of: oleyl alcohols, dodecylsulfate, dodecylsulfonate or other anionic surfactants, nonionic surfactants such as fatty alcohol ethers, cocamidopropyl betaine or other ampholytic surfactants, and any combination thereof. In an embodiment of the dyeing agent of the present invention, the penetration enhancing agent can be a single or a mixture of oleyl alcohol, dodecylsulfate or other anionic surfactants, nonionic surfactants such as fatty alcohol ethers, cocamidopropyl betaine or other ampholytic surfactants. According to the dyeing agent of the present invention, the penetration enhancing agent can be a single penetration enhancing agent, or any combination of a plurality of penetration enhancing agents. In an embodiment of the dyeing agent of the present invention, the penetration enhancing agent constitutes 2-15% (wt) of the total weight of the dyeing agent. In an embodiment of the dyeing agent of the present invention, the penetration enhancing agent constitutes 3-10% (wt) of the total weight of the dyeing agent.

The dyeing agent according to any item of the third aspect of the present invention further comprises a thickening agent (i.e., a viscosity regulator for regulating the state of fluid such as liquid, semi-solid, etc.). In an embodiment of the dyeing agent of the present invention, the thickening agent includes but is not limited to one or more of fatty alcohols or polymers such as carbomers, hydroxyethylcellulose, and hydroxypropylcellulose. In an embodiment of the dyeing agent of the present invention, the weight percentage of the thickening agent in the dyeing agent can be determined by those skilled in the art according to the teachings of the present application in combination with the prior art. Preferably, in an embodiment of the dyeing agent of the present invention, the thickening agent constitutes 1-10% (wt) of the total weight of the dyeing agent. In an embodiment of the dyeing agent of the present invention, the thickening agent constitutes 2-8% (wt) of the total weight of the dyeing agent.

The dyeing agent of any item of the third aspect of the present invention is present in the form of emulsion, paste or gel.

The fourth aspect of the present invention provides a method for dyeing hair by using the hair dyeing product of any item of the second aspect of the present invention, comprising:
a) a step of treating the hair by applying the softening agent to the hair; and
b) a step of treating the hair by applying the mordant and the dyeing agent to the hair in any order.

According to the method of any item of the fourth aspect of the present invention, the item a) further comprises: keeping the softening agent at a suitable temperature for a suitable period of time after it is applied to the hair. In an embodiment, the item a) further comprises: keeping the softening agent at 15-60° C. (preferably 20-40° C.) for 5-60 min (preferably 20-40 min, preferably 20-30 min) after it is applied to the hair.

According to the method of any item of the fourth aspect of the present invention, the item b) further comprises: keeping the mordant at a suitable temperature for a suitable period of time after it is applied to the hair. In an embodiment, the item b) further comprises: keeping the mordant at 15-60° C. (preferably 20-40° C.) for 5-30 min (preferably 5-25 min, preferably 10-20 min) after it is applied to the hair.

According to the method of any item of the fourth aspect of the present invention, the item b) further comprises: keeping the dyeing agent at a suitable temperature for a suitable period of time after it is applied to the hair. In an embodiment, the item b) further comprises: keeping the dyeing agent at 15-60° C. (preferably 20-40° C.) for 2-20 min (preferably 5-15 min, preferably 8-12 min) after it is applied to the hair.

The method according to any item of the fourth aspect of the present invention further comprises at least one of the following treatment steps:

a step of treating the hair by repeatedly applying uniformly the softening agent to the hair, and an optional step of washing the hair with water after the treatment;

a step of treating the hair by repeatedly applying uniformly the mordant to the hair, and an optional step of washing the hair with water after the treatment; and a step of treating the hair by repeatedly applying uniformly the mordant to the hair, and an optional step of washing the hair with water after the treatment.

The fifth aspect of the present invention provides a method for dyeing hair by using the hair dyeing product of any item of the second aspect of the present invention, comprising at least one of the following treatment items i to iii:

i (1) a step of treating the hair by applying the softening agent to the hair; and (2) a step of treating the hair by mixing the mordant and the dyeing agent before use and then applying the mixture to the hair; or ii (1) a step of treating the hair by mixing the softening agent and the mordant before use and then applying the mixture to the hair; and (2) a step of treating the hair by applying the dyeing agent to the hair; or iii (1) a step of treating the hair by mixing the softening agent and the dyeing agent before use and then applying the mixture to the hair; and (2) a step of treating the hair by applying the mordant to the hair.

According to the method of any item of the fifth aspect of the present invention, in at least one of the items i to iii, the step (1) comprises: keeping the softening agent, the mixture of the softening agent and the mordant, or the mixture of the softening agent and the dyeing agent at 15-60° C. (preferably 20-40° C.) for 10-40 min (preferably 15-35 min, preferably 20-30 min) after it is applied to the hair.

According to the method of any item of the fifth aspect of the present invention, in at least one of the items i to iii, the step (2) comprises: keeping the mixture of the mordant and the dyeing agent, the dyeing agent, or the mordant at 15-60° C. (preferably 20-40° C.) for 2-30 min (preferably 5-25 min, preferably 10-20 min) after it is applied to the hair.

The method according to any item of the fifth aspect of the present invention further comprises at least one of following steps of treatment:

a step of treating the hair by repeatedly applying uniformly the softening agent to the hair, and an optional step of washing the hair with water after the treatment;

a step of treating the hair by repeatedly applying uniformly the mordant to the hair, and an optional step of washing the hair with water after the treatment;

a step of treating the hair by repeatedly applying uniformly the dyeing agent to the hair, and an optional step of washing the hair with water after the treatment;

a step of treating the hair by repeatedly applying uniformly the mixture of the softening agent and the dyeing agent to the hair, and an optional step of washing the hair with water after the treatment;

a step of treating the hair by repeatedly applying uniformly the mixture of the softening agent and the mordant to the hair, and an optional step of washing the hair with water after the treatment; and a step of treating the hair by repeatedly applying uniformly the mixture of the mordant and the dyeing agent to the hair, and an optional step of washing the hair with water after the treatment.

The terms used herein have their common meanings in the art, and, particularly, unless indicated otherwise, the following terms in the present invention have the meanings as defined below.

As used herein, the term "hair", hairs", or "hairs of head" generally refers to hair of an animal (e.g., a mammal such as pets, and human, especially human). It particularly refers to the hair on head of the animals, especially the hair on head of human.

As used herein, the term "hair dyeing product" generally refers to a product for coloring the hair of an animal (e.g., a mammal such as pets, and human, especially human). In the present invention, since the dye (iron gallate) is of block color, the "hair dyeing product" of the present invention can also be referred to herein as "darkening product" in this regard.

As used herein, the term "step of treating the hair by applying the mordant and the dyeing agent to the hair in any order" means when the mordant and the dyeing agent are used to treat the hair, the order (sequence) of using the mordant and the dyeing agent is arbitrary.

As used herein, the term "mordant" usually refers to a composition to allow for a dyeing agent to dye an article (such as a textile or hair) to be dyed through a medium, thereby fulfilling the dyeing purpose. In the present invention, since the ferric ions for forming pigments with the dye molecule gallic acid by way of complexation is generated from ferrous ions by air oxidation, the composition comprising ferrous ions can also be referred to herein as "mordant". In brief, the mordant can also be referred to herein as the second component to be distinguished from the first component as the softening agent and the third component as the dyeing agent. In addition, the above mentioned "the first component", "the second component" and "the third component" are used merely for distinguishing between each other, and do not relate to any relation, such as order, sequence, size, amount, importance or the like. However, the three parts as called "the first component", "the second component" and "the third component" can separately bring about softening, mordanting and dyeing effects during a hair dyeing process. Further, according to the hair dyeing product as provided in the second aspect of the present invention, before it is produced, stored, transported and sold to an end user, the abovementioned three parts: "the first component", "the second component" and "the third component" are physically isolated, before the three components are finally used, they can be mixed according to the method of the fourth aspect or the fifth aspect of the present invention. In general, according to the spirit of the present invention, the hair dyeing product as provided in the second aspect of the present invention can be used in two ways: one is that the aforementioned three parts: the first component, the second component and the third component are used in a certain sequence to treat the hair separately;

another is that any two of the three parts: the first component, the second component and the third component are mixed just before being used and then the mixture is used to treat hair, and the residual one is then used to treat hair. During the course of dyeing hair using the hair dyeing product of the present invention, the softening agent, mordant, and dyeing agent of the hair dyeing product of the present invention can be used at least in any of the following combinations:

1: step (1) applying the softening agent to a hair, keeping for 20-30 min, washing or not washing the hair; step (2) applying the mordant to the hair, keeping for 10-20 min, washing the hair; and step (3) applying the dyeing agent to the hair, keeping for 10 min, washing the hair;

2: step (1) applying the softening agent to a hair, keeping for 20-30 min, washing or not washing the hair; step (2) applying the dyeing agent to the hair, keeping for 10-20 min, washing the hair; and step (3) applying the mordant to the hair, keeping for 10 min, washing the hair;

3: step (1) applying the softening agent to a hair, keeping for 20-30 min, washing or not washing the hair; and step (2) mixing the mordant and the dyeing agent in a certain ratio in advance and then applying to the hair, keeping for 10-20 min, washing the hair;

4: step (1) mixing the softening agent and the mordant in a certain ratio in advance and then applying to a hair, keeping for 20-30 min, washing the hair; and step (2) applying the dyeing agent to the hair, keeping for 10-20 min, washing the hair;

5: step (1) mixing the softening agent and the dyeing agent in a certain ratio in advance and then applying to a hair, keeping for 20-30 min, washing the hair; and step (2) applying the mordant to the hair, keeping for 10-20 min, washing the hair.

In addition, when any two of the aforementioned three parts: the first component, the second component and the third component are mixed before use, the ratio (by weight) of the mixed two components can be: (0.1-10): 1, preferably (0.2-8): 1, preferably (0.5-5): 1, preferably (0.8-2): 1, such as about 0.5:1, about 0.8:1, about 1:1, about 1.2:1, about 1.5:1, about 1.8:1, or about 2:1.

As used herein, the term "ferrous salt" generally refers to a salt formed by ferrous ion (i.e., bivalent iron ion). Some illustrative examples of the ferrous salt of the present invention include ferrous sulfate, ferrous chloride, and ferrous nitrate. Those skilled in the art clearly know that the ferrous salt can also extend to the ferrous salts formed in situ by chemical conversion from ferrous compounds, i.e., the ferrous salt can also extend to cover the ferrous compounds, for example, ferrous oxide can be converted in situ using hydrochloric acid to form ferrous chloride as ferrous salt, so the ferrous oxide can also be deemed as the ferrous salt of the present invention.

As used herein, the term "effective amount" generally refers to an amount of the substance to be discussed, for example, the amount of a ferrous salt in the mordant, which is sufficient to achieve substantially desired or expected hair dyeing effects under general application conditions.

As used herein, the term "antioxidant" refers to a substance capable of prevent a readily oxidizable substance from being oxidized. For example, the antioxidant used in the mordant of the present invention can prevent the oxidation of a ferrous salt therein.

As used herein, the term "penetration enhancing agent" generally refers to a substance used for enhancing the penetration of another substance, and also referred to herein as a penetration enhancer. For example, the penetration enhancing agent used in the mordant of the present invention can accelerate the rate that ferrous salt enters inside of hair.

As used herein, the term "thickening agent" generally refers to a substance used for regulating the viscosity of fluid (such as liquid, semi-solid, etc.), usually increasing the viscosity of fluid, and can also be referred to herein as a viscosity regulator.

The three parts: the mordant, softening and dyeing agents of the present invention can be present in the form of emulsion, paste or gel. According to the present invention, the three parts can also be present in other forms, such as in the form of solution.

As used herein, the term "softening agent" generally refers to a composition capable of softening cuticular keratin of hair. In the present invention, a composition comprising disulfide bond reducing agent and alkalizing agent and being capable of softening and swelling hair is called "softening agent".

As used herein, the term "dyeing agent" generally refers to a composition capable of dyeing fiber and other materials. In the present invention, a composition comprising an active dye substance and accessory ingredients for enhancing dyeing effect and being capable of dyeing hair is called "dyeing agent".

As used herein, the term "active dye substance" generally refers to an active ingredient capable of dyeing a fiber, hair and other materials, which is different from the accessory ingredients used for achieving better effects of the present invention. In the present invention, the active dye substance refers to a substance that per se does not contain a metal ion for mordanting and can complex with a metal ion obtained by treating hair with the mordant before and after hair dyeing to dye hair. In the text, the "active dye substance" particularly refers to substances such as gallic acid and ester thereof.

As used herein, the term "stabilizing agent" generally refers to a substance capable of stabilizing other substances. For example, the "stabilizing agent" used in the dyeing agent can make the active dye substance such as gallic acid therein more physically or chemically stable.

As used herein, the term "disulfide bond reducing agent" generally refers to a reducing agent capable of reducing the disulfide bond (—S—S—) of hair to —SH, thereby relaxing tension and facilitating the penetration of active substance into hair. The examples include acetylcysteine or derivatives thereof in the present invention. The examples of disulfide bond reducing agent are disclosed in detail in the text.

As used herein, especially used in the softening agent in the present invention, the term "alkalizing agent" generally refers to a substance allowing for the obtained product to reach a certain pH value. For example, in an embodiment of the hair dyeing product of the present invention, the alkalizing agent in the softening agent makes the pH value of the softening agent to be less than 7; or, for example, the alkalizing agent in the softening agent makes the pH value of the softening part to be less than 8; or, for example, the alkalizing agent in the softening agent makes the pH value of the softening part to be less than 9; or, for example, the alkalizing agent in the softening agent makes the pH value of the softening part to be less than 10; or, for example, the alkalizing agent in the softening agent makes the pH value of the softening part to be less than 11. The pH value can be directly measured by using pH paper, or by any method known in the art, such as pH meter assay, optionally, the measurement is performed after a suitable treatment, for example, properly diluting with water.

As used herein, the term "main component" generally refers to the active component in a composition, for example, in the mordant useful in hair dyeing product provided in the first aspect of the present invention, the ferrous salt as active component can be defined as "main component". In view of "main component", the other components in the composition can be deemed "accessory components", for example, the antioxidant in the mordant of the present invention can be referred to herein as "accessory component".

As for the mordant of the present invention as well as the softening agent and the dyeing agent in the hair dyeing product of the present invention, the methods for their preparation can be readily carried out by those skilled in the art according to associated textbooks, for example, the preparation can be carried out by processing steps such as mixing, heating, stirring, milling, emulsifying, metered volume, subpackaging. For example, the procedures of formulation can be conducted according to the methods taught in the chapters about solutions, emulsions, and pastes, etc. of *Pharmacy*, Edited by Xi Nianzhu, People's Health Publishing House, Beijing, 1994, and this textbook is incorporated herein by reference.

The mordant of the present invention and the hair dyeing product comprising the mordant do not contain thioglycolic acid, aromatic compounds such as p-phenylenediamine and hydrogen peroxide, and thus are safe and free of irritation and has no potential carcinogenicity. It was found that the allergizing rate was 0% when it was applied to subjects with white hair; the dyed hair was present in natural black color and kept for about 45 days with good fastness. In addition, ferrous ions are used as active component in the mordant of the present invention, which ensures the stability of product and the dyeing effects within marketabie life. Further, the hair dyeing product of the present invention can be added with hair cleaning and hair care components in the softening agent and dyeing agent, and it is not necessary to wash hair for many times during hair dyeing procedure. Hence, the hair dyed with the hair dyeing product of the present invention has good chromaticity and fastness as well as natural gloss, and the stability and convenience of the product in use are also very good.

CONCRETE MODES FOR CARRYING OUT THE INVENTION

The present invention is further illustrated with working examples, comparative examples and test examples as follows. It should be understood that these working examples, comparative examples and test examples are merely used for illustrating the present invention, but not intended to limit the present invention in any way.

The materials and methods used in the examples are described generally and/or specifically in the present invention. Although many materials and methods used in the present invention are well known in the art, they are still described in detail as much as possible. Those skilled in the art well know in the context, if not particularly described, the materials and methods used in the present invention are well-known in the art.

EXAMPLE 1

1) The softening agent (or referred to herein as the first component, formulated in a total amount of 100 g): 6 g of N-acetylcysteine, 1 g of sodium sulfite, 4 g of sodium dodecylsulfate, 0.5 g of carbomer, 0.2 g of hydantoin were mixed uniformly, then a mixture of arginine and monoethanolamine (arginine:monoethanolamine=1:1 (weight ratio)) was added for regulating pH to have a final pH of 9.5 (test strips), then deionized water was added to reach 100 g, and mixed uniformly by stirring to obtain a gel.

2) The mordant (or referred to herein as the second component, formulated in a total amount of 100 g): 5 g of cetearyl alcohol, 5 g of ceteareth-6, 0.25 g of methyl paraben, 0.15 g of ethyl paraben, 5 g of ferrous sulfate, 0.5 g of cysteine were mixed uniformly, then deionized water as balance was added, and mixed uniformly by stirring to obtain a paste.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 6 g of gallic acid, 0.2 g of sodium sulfite, 0.2 g of disodium ethylenediamine tetraacetate, 0.25 g of methyl paraben, 0.15 g of propyl paraben were mixed uniformly, then deionized water as balance was added, and mixed uniformly by stirring to obtain a paste.

4) Hair dyeing test of hair bundle: Hair was used without being washed, to which the softening agent was directly applied uniformly by a hair comb repeatedly, and kept for 20-30 min. The hair was not washed, to which the mordant was applied uniformly according to the method of applying the softening agent, and kept for 10-20 min. The hair was then washed with a small quantity of warm water, and wiped until no water dropped. The dyeing agent was applied to the hair uniformly according to the methods of applying the former two agents, kept for 10 min, the hair was washed with warm water, and air dried or blow dried. The results showed that the hair bundle dyed with the hair dyeing product of the present example had a good color chroma and fastness, and the preparation was stable.

In the following Examples 1-1, 2, 2-1, 3, 3-1, 4, and 5, only the formulae of the softening, mordant and dyeing agents were given, and the procedures of foumulation thereof were carried out according to those of Example 1.

EXAMPLE 1-1

1) The softening agent (or referred to herein as the first component, formulated in a total amount of 100 g): 6 g of N-acetylcysteine, 1 g of sodium sulfite, 4 g of sodium dodecylsulfate, 0.5 g of carbomer, arginine:monoethanolamine=1:1 (weight ratio), final pH of product=9.5 (test strips), balanced with deionized water, mixed by stirring, processed to obtain a gel.

2) The mordant (or referred to herein as the second component, formulated in a total amount of 100 g): 5 g of cetearyl alcohol, 5 g of ceteareth-6, 0.25 g of methyl paraben, 0.15 g of ethyl paraben, 5 g of ferrous sulfate, 0.5 g of cysteine, balanced with deionized water, mixed by stirring, processed to obtain a paste.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 6 g of gallic acid, 0.2 g of sodium sulfite, 0.2 g of disodium ethylenediamine tetraacetate, 0.25 g of methyl paraben, 0.15 g of propyl paraben, balanced with deionized water, processed to obtain a paste.

4) Hair dyeing test of hair bundle: Hair was used without being washed, to which the softening agent was directly applied uniformly by a hair comb repeatedly, and kept for 20-30 min. The hair was not washed, to which the mordant was applied uniformly according to the method of applying the softening agent, and kept for 10-20 min. The hair was then washed with a small quantity of warm water, and wiped until no water dropped. The dyeing agent was applied to the hair uniformly according to the methods of applying the former two agents, kept for 10 min, the hair was washed with warm water, and air dried or blow dried. The results showed that the hair bundle dyed with the hair dyeing product of the present example had a good color chroma and fastness, and the preparation was stable.

EXAMPLE 2

1) The softening agent (or referred to herein as the first component, formulated in a total amount of 100 g): 1.5 g of cysteine, 0.5 g of sodium sulfite, 4 g of sodium dodecylsulfate, 6 g of sodium laureth sulfate, 0.5 g of carbomer, 0.2 g of hydantoin, arginine:monoethanolamine=1:1 (weight ratio) having an amount to reach a final pH of product=10.5 (test strips), and the balance being deionized water.

2) The mordant (or referred to herein as the second component, formulated in a total amount of 100q): 1 g of cetearyl alcohol, 10 g of ceteareth-6, 10 g of ferrous chloride, 2 g of acetylcysteine, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 15 g of gallic acid, 1 g of sodium sulfite, 0.5 g of disodium ethylenediamine tetraacetate, 0.25 g of methyl paraben, 0.15 g of propyl paraben, and the balance being deionized water.

4) Hair dyeing test of hair bundle: Hair was used without being washed, to which the softening agent was directly applied uniformly by a hair comb repeatedly, and kept for 20-30 min. The hair was not washed, the dyeing agent was applied to the hair uniformly according to the method of applying the softening agent, and kept for 10-20 min. The hair was then washed with a small quantity of warm water, and wiped until no water dropped. The mordant was applied to the hair uniformly according to the methods of applying the former two agents, kept for 10 min, the hair was washed with warm water, and air dried or blow dried.

The results showed that the hair bundle dyed with the hair dyeing product of the present example had a good color chroma and fastness, and the preparation was stable.

EXAMPLE 2-1

1) The softening agent (or referred to herein as the first component, formulated in a total amount of 100 g): 1.5 g of cysteine, 0.5 g of sodium sulfite, 4 g of sodium dodecylsulfate, 6 g of sodium laureth sulfate, 0.5 g of carbomer, arginine:monoethanolamine=1:1 (weight ratio) having an amount to reach a final pH of product=10.5 (test strips), and the balance being deionized water.

2) The mordant (or referred to herein as the second component, formulated in a total amount of 100 g): 1 g of cetearyl alcohol, 10 g of ceteareth-6, 10 g of ferrous chloride, 2 g of acetylcysteine, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 15 g of gallic acid, 1 g of sodium sulfite, 0.5 g of disodium ethylenediamine tetraacetate, 0.25 g of methyl paraben, 0.15 g of propyl paraben, and the balance being deionized water.

4) Hair dyeing test of hair bundle: Hair was used without being washed, to which the softening agent was directly applied uniformly by a hair comb repeatedly, and kept for 20-30 min. The hair was not washed, the dyeing agent was applied to the hair uniformly according to the method of applying the softening agent, and kept for 10-20 min. The hair was then washed with a small quantity of warm water, and wiped until no water dropped. The mordant was applied to the hair uniformly according to the methods of applying the former two agents, kept for 10 min, the hair was washed with warm water, and air dried or blow dried.

The results showed that the hair bundle dyed with the hair dyeing product of the present example had a good color chroma and fastness, and the preparation was stable.

EXAMPLE 3

1) The softening agent (or referred to herein as the first component, formulated in a total amount of 100 g): 24 g of N-acetylcysteine, 1 g of sodium sulfite, 2 g of sodium dodecylsulfate, 2 g of cocamidopropylbetaine, 0.5 g of carbomer, 0.2 g of hydantoin, arginine:monoethanolamine=1:1 (weight ratio) having an amount to reach a final pH of product=8.5 (test strips), and the balance being deionized water.

2) The mordant (or referred to herein as the second component, formulated in a total amount of 100 g): 10 g of cetearyl alcohol, 1 g of ceteareth-6, 0.5 g of ferrous nitrate, 0.1 g of cysteine hydrochloride, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 0.25 g of methyl paraben, 0.15 g of propyl paraben, 0.5 g of gallic acid, 0.05 g of sodium sulfite, 0.05 g of disodium ethylenediamine tetraacetate, and the balance being deionized water.

4) Hair dyeing test of hair bundle: Hair was used without being washed, to which the softening agent was directly applied uniformly by a hair comb repeatedly, and kept for 20-30 min. The hair was washed, the mordant and the dyeing agent were mixed in a ratio of 1:1, the mixture was applied to the hair uniformly according to the method of applying the softening agent, and kept for 10-20 min. The hair was then washed with warm water, and air dried or blow dried.

The results showed that the hair bundle dyed with the hair dyeing product of the present example had a good color chroma and fastness, and the preparation was stable.

EXAMPLE 3-1

1) The softening agent (or referred to herein as the first component, formulated in a total amount of 100 g): 24 g of N-acetylcysteine, 1 g of sodium sulfite, 2 g of sodium dodecylsulfate, 2 g of cocamidopropylbetaine, 0.5 g of hydroxyethylcellulose, arginine:monoethanolamine=1:1 (weight ratio) having an amount to reach a final pH of product=8.5 (test strips), and the balance being deionized water.

2) The mordant (or referred to herein as the second component, formulated in a total amount of 100 g): 10 g of cetearyl alcohol, 1 g of ceteareth-6, 0.5 g of ferrous nitrate, 0.1 g of cysteine hydrochloride, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 5 g of ceteareth-6, 2 g of sodium dodecylsulfate, 2 g of lanolin, 2 g of albolene, 0.25 g of methyl paraben, 0.15 g of propyl paraben, 0.5 g of gallic acid, 0.05 g of sodium sulfite, 0.05 g of disodium ethylenediamine tetraacetate, and the balance being deionized water.

4) Hair dyeing test of hair bundle: Hair was used without being washed, to which the softening agent was directly applied uniformly by a hair comb repeatedly, and kept for 20-30 min. The hair was washed, the mordant and the dyeing agent were mixed in a ratio of 1:1, the mixture was applied to the hair uniformly according to the method of applying the softening agent, and kept for 10-20 min. The hair was then washed with warm water, and air dried or blow dried.

The results showed that the hair bundle dyed with the hair dyeing product of the present example had a good color chroma and fastness, and the preparation was stable.

EXAMPLE 4

1) The softening agent (or referred to herein as the first component, formulated in a total amount of 100 g): 24 g of N-acetylcysteine, 1 g of sodium sulfite, 1 g of sodium dodecylsulfate, 1 g of xanthan gum, arginine:monoethanolamine=1:1 (weight ratio) having an amount to reach a final pH of product=9.5 (test strips), and the balance being deionized water.

2) The mordant (or referred to herein as the second component, formulated in a total amount of 100 g): 10 g of cetearyl alcohol, 5 g of ceteareth-6, 5 g of ferrous gluconate, 0.8 g of cysteine hydrochloride, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 1 g of ceteareth-6, 2 g of sodium dodecylsulfate, 2 g of lanolin, 2 g of albolene, 0.25 g of methyl paraben, 0.15 g of propyl paraben, 0.5 g of gallic acid, 0.05 g of sodium sulfite, 0.05 g of disodium ethylenediamine tetraacetate, and the balance being deionized water.

4) Hair dyeing test of hair bundle: Hair was used without being washed, the softening agent and the mordant were mixed in a ratio of 1:1 in advance, the mixture was directly applied to the hair uniformly by a hair comb repeatedly, and kept for 20-30 min. The hair was washed, to which the dyeing agent was applied uniformly by combing, and kept for 10-20 min. The hair was then washed with warm water, and air dried or blow dried.

The results showed that the hair bundle dyed with the hair dyeing product of the present example had a good color chroma and fastness, and the preparation was stable.

EXAMPLE 5

1) The softening agent (or referred to herein as the first component, formulated in a total amount of 100q): 24 g of N-acetylcysteine, 1 g of sodium sulfite, 1 g of cocamidopropylbetaine, 0.1 g of hydroxypropylmethylcellulose, arginine:monoethanolamine=1:1 (weight ratio) having an amount to reach a final pH of product=10.5 (test strips), and the balance being deionized water.

2) The mordant (or referred to herein as the second component, formulated in a total amount of 100 g): 10 g of cetearyl alcohol, 3 g of ceteareth-6, 0.5 g of ferrous lactate, 0.1 g of cysteine hydrochloride, 0.25 g of methyl paraben, 0.15 g of propyl paraben, and the balance being deionized water.

3) The dyeing agent (or referred to herein as the third component, formulated in a total amount of 100 g): 5 g of cetearyl alcohol, 3 g of ceteareth-6, 2 g of sodium dodecylsulfate, 2 g of lanolin, 2 g of albolene, 0.25 g of methyl paraben, 0.15 g of propyl paraben, 0.5 g of gallic acid, 0.05 g of sodium sulfite, 0.05 g of disodium ethylenediamine tetraacetate, and the balance being deionized water.

4) Hair dyeing test of hair bundle: Hair was used without being washed, the softening agent and the dyeing agent were mixed in a ratio in advance, the mixture was directly applied to the hair uniformly by a hair comb repeatedly, and kept for 20-30 min. The hair was washed, to which the mordant was applied uniformly by combing, and kept for 10-20 min. The hair was then washed with warm water, and air dried or blow dried.

The results showed that the hair bundle dyed with the hair dyeing product of the present example had a good color chroma and fastness, and the preparation was stable.

COMPARATIVE EXAMPLE 1

Preparation of a Hair Dyeing Product According to the Method of CN1593375A

1) The softening agent (formulated in a total amount of 100q): 2.0 g of N-acetylcysteine, 0.5 g of sodium sulfite, 2.0 g of sodium carboxymethylcellulose, 0.1 g of disodium ethylenediamine tetraacetate, 10.0 g of monoethanolamine, and 85.4 g of deionized water were mixed until dissolution complete.

2) The dyeing agent (formulated in a total amount of 100 g): 2.0 g of gardenia yellow, 5.0 g of sodium carboxylmethylcellulose, 1.0 g of sodium dodecylsulfate, and 92 g of deionized water were stirred until dissolution complete.

3) The mordant (formulated in a total amount of 100 g): 3 g of ferric chloride, 3 g of xanthan gum, and 94 g of deionized water were stirred until dissolution complete to obtain the mordant.

4) Hair dyeing test of hair bundle: Hair was washed and then the water on the hair was wiped, the treating agent was applied to the hair uniformly, heated to 35-45° C., and kept for 15-25 min. The dyeing agent was applied to the hair uniformly, heated to 35-45° C., kept for 5-10 min. The mordant was finally applied to the hair, heated to 35-45° C., and kept for 4-8 min. The hair was washed with warm water.

COMPARATIVE EXAMPLE 2

Preparation of a Hair Dyeing Product According to the Method of CN1401310A

1) The softening agent (formulated in a total amount of 100 g): 10 g of DL-cysteine hydrochloride, 4 g of ethanolamine, 2 g of fatty alcohol, 3 g of albolene, 1 g of fatty alcohol-polyoxyethylene ether, 3 g of polyoxyethylene sorbitan monostearate, 1 g of alkylsulfate salt, 3 g of glyceryl monostearate, 3 g of sorbitan monostearate, 70 g of purified water were mixed by stirring.

2) The mordant (formulated in a total amount of 100 g): 5 g of ferric sulfate, 4 g of carboxylmethylcellulose, 91 g of purified water were stirred until dissolution complete.

3) The dyeing agent (formulated in a total amount of 100 g): 3 g of gallic acid, 4 g of ethanolamine, 3 g of albolene, 1 g of fatty alcohol-polyoxyethylene ether, 2 g of polyoxyethylene sorbitan monostearate, 3 g of glyceryl monostearate, 3 g of sorbitan monostearate, 76 g of purified water were mixed by stirring.

4) Hair dyeing test of hair bundle: Hair was wetted with water and the water on the hair was wiped, the softening agent was directly applied to the hair uniformly by a hair comb repeatedly, and kept for 20-30 min. The hair was not washed, to which the mordant was applied uniformly according to the method of applying the softening agent, kept for 15-30 min. The hair was then washed with a small quality of warm water, and wiped until no water dropped. The dyeing agent was uniformly applied to the hair according to the methods of applying the former agents, kept for 10-20 min. The hair was washed with warm water, and air dried or blow dried.

TEST EXAMPLE 1

Tests of Hair Bundle Chromaticity and Fastness and Stability of the Preparations 1) Test methods:

Hair bundle chromaticity: the dyed hair was measured with colorimeter, and observed with naked eye.

Hair bundle fastness: the dyed hair was exposed to sunlight to observe its sunlight fastness; and the dyed hair was washed with commercial shampoo to observe its washing resistance fastness.

Stability of product: the samples were stored in a baking oven at 45° C. for two weeks, then stored in a refrigerator at −10° C., and the samples were observed in term of state and used in dyeing test.

2) Test results:

Three preparations of Example 1, Comparative Example 1 and Comparative 2 were used for hair dyeing according to the methods thereof, and their stabilities were observed:

The hair dyeing results of the hair dyeing product of Example 1 showed that black was measured by colorimeter, and also observed by naked eye; fastness was observed after being exposed to sunlight for 45 days and being washed for 45 times. The three parts: softening agent, mordant and dyeing agent were all subjected to stability test, and their appearances did not obviously change before and after test, and the hair dyeing results did not change as well.

The hair bundle dyeing results of the hair dyeing product of Comparative Example 1 showed that a non-black color with a slight yellowish tint was observed by colorimeter, and yellow color was observed by naked eye; in the fastness test, color fading was observed after being exposed to sunlight for 10 days and after being washed for 5 times. The three parts: softening agent, mordant and dyeing agent were all subjected to stability test, and their appearances did not obviously change before and after the test, trivalent iron was active substance in the mordant and deposit occurred in the part, with the lapse of time, deposit became more and more and the color became darker and darker, the hair dyeing resulted in pale yellow.

The hair bundle dyeing results of the hair dyeing product of Comparative Example 2 showed that a non-black color with a slight yellowish tint was observed by colorimeter, and light purple color was observed by naked eye; in the fastness test, color fading was observed after being exposed to sunlight for 10 days and after being washed for 10 times. The three parts: softening agent, mordant and dyeing agent were all subjected to stability test, the appearances of the softening agent and the dyeing agent did not obviously change before and after the test, trivalent iron was active substance in the mordant and deposit occurred in the part, with the lapse of time, deposit became more and more and the color became darker and darker, the hair dyeing resulted in a much light purple.

In addition, after the hair dyeing product of Example 1 of the present invention was applied to a subject with white hair, the results showed the dyed hair was of natural black color, the fastness was kept for about 45 days, and the allergizing rate was 0%.

The inventors of the present invention have also found that after the samples as prepared in other examples of the present application were subjected to the above method of Test Example 1, the results were also satisfactory, and similar to those of the sample of Example 1.

What is claimed is:

1. A mordant useful in a dyeing hair product, comprising an effective amount of a ferrous salt and an antioxidant.

2. The mordant of claim 1, wherein the ferrous salt is ferrous sulfate, ferrous chloride, ferrous nitrate, ferrous gluconate, ferrous lactate, ferrous fumarate, or a combination thereof.

3. The mordant of claim 2, wherein the ferrous salt constitutes 0.5-10% (wt) of the total weight of the mordant.

4. The mordant of claim 1, wherein the antioxidant is ascorbic acid or salts thereof, cysteine or derivatives thereof or salts thereof, a reduced glutathione, or a combination thereof.

5. The mordant of claim 4, wherein the antioxidant constitutes 0.1-2% (wt) of the total weight of the mordant.

6. The mordant of claim 1, further comprising water, a penetration enhancing agent, a thickening agent, a preservative, or a combination thereof.

7. A hair dyeing product, comprising a softening agent, a dyeing composition, wherein the dyeing composition comprises a dyeing agent and the mordant of claim 1.

8. The hair dyeing product of claim 7, wherein the dyeing agent comprises an effective amount of an active dye substance and optionally water.

9. The hair dyeing product of claim 8, wherein the active dye substance in the dyeing agent is gallic acid, or salts or esters thereof, or a combination thereof.

10. The hair dyeing product of claim 9, wherein the active dye substance in the dyeing agent constitutes 0.5-15% (wt) of the total weight of the dyeing agent.

11. The hair dyeing product of claim 8, wherein the dyeing agent further comprises a stabilizing agent, a penetration enhancing agent, a thickening agent, or a combination thereof.

12. The hair dyeing product of claim 7, wherein the softening agent comprises an effective amount of a disulfide bond reducing agent and an alkalizing agent.

13. The hair dyeing product of claim 12, wherein:
 i) the disulfide bond reducing agent in the softening agent is cysteine or derivatives thereof or their salts, acetylcysteine or derivatives thereof or their salts, a sulfite, or a bisulfite, or any combination thereof
 ii) the alkalizing agent in the softening agent is ornithine, arginine, lysine, ammonia, an ethanolamine, an alkanolamide, or a composition comprising a carbonate, or any combination thereof and/or
 iii) the softening agent further comprises one or more components that is water, a penetration enhancing agent, or a thickening agent.

14. The hair dyeing product of claim 7 further comprising an information material regarding a method for using the hair dyeing product.

15. The hair dyeing product of claim 14, wherein the information material comprises the following information:
 a) a step of treating the hair by applying the softening agent to the hair; and
 b) a step of treating the hair by applying the mordant and the dyeing agent to the hair in any order.

16. The hair dyeing product of claim 14, wherein the information material comprises any one of the following items i to iii:
 i (1) a step of treating the hair by applying the softening agent to the hair, and (2) a step of treating the hair by mixing the mordant and the dyeing agent before use and then applying the mixture to the hair; or
 ii (1) a step of treating the hair by mixing the softening agent and the mordant before use and then applying the mixture to the hair; and (2) a step of treating the hair by applying the dyeing agent to the hair; or iii (1) a step of treating the hair by mixing the softening agent and the dyeing agent before use and then applying the mixture to the hair; and (2) a step of treating the hair by applying the mordant to the hair.

17. A dyeing composition, comprising a dyeing agent and the mordant of claim 1, wherein the dyeing agent comprises an effective amount of an active dye substance, and optionally water, a stabilizing agent, a penetration enhancing agent, a thickening agent, or a combination thereof; wherein the active dye substance is gallic acid or salts or esters thereof.

18. A method for dyeing hair by using the hair dyeing product of claim 7, comprising:
   a) a step of treating the hair by applying the softening agent to the hair; and
   b) a step of treating the hair by applying the mordant and the dyeing agent to the hair in any order.

19. A method for dyeing hair using the hair dyeing product of claim 7 comprising any one of the following items i to iii:
   i (1) a step of treating the hair by applying the softening agent to the hair; and (2) a step of treating the hair by mixing the mordant and the dyeing agent before use and then applying the mixture to the hair; or
   ii (1) a step of treating the hair by mixing the softening agent and the mordant before use and then applying the mixture to the hair; and (2) a step of treating the hair by applying the dyeing agent to the hair; or
   iii (1) a step of treating the hair by mixing the softening agent and the dyeing agent before use and then applying the mixture to the hair; and (2) a step of treating the hair by applying the mordant to the hair.

20. The mordant of claim 4, wherein the antioxidant is sodium ascorbate, cysteine hydrochloride, N-acetylcysteine, or a combination thereof.

21. The mordant of claim 4, wherein the antioxidant is D-cysteine, L-cysteine, DL-cysteine, N-acetylcysteine, or salts thereof, or a combination thereof.

22. The hair dyeing product of claim 9, wherein the active dye substance in the dyeing agent is gallic acid methyl ester, gallic acid ethyl ester, gallic acid propyl ester, or combinations thereof.

23. The dyeing agent of claim 17, wherein the active dye substance is gallic acid methyl ester, gallic acid ethyl ester, gallic acid propyl ester, or any combination thereof.

24. The hair dyeing product of claim 13, wherein the ethanolamine is monoethanolamine, diethanolamine, triethanolamine, or a combination thereof.

* * * * *